(12) United States Patent
Hök

(10) Patent No.: US 7,146,857 B2
(45) Date of Patent: Dec. 12, 2006

(54) REAL TIME ANALYSIS FOR GAS MIXTURES

(75) Inventor: Bertil John Waldemarsson Hök, Västerås (SE)

(73) Assignee: Hok Instrument AB, Vasteras (SE)

( * ) Notice: Subject to any disclaimer, the term of this patent is extended or adjusted under 35 U.S.C. 154(b) by 56 days.

(21) Appl. No.: 10/990,739

(22) Filed: Nov. 16, 2004

(65) Prior Publication Data

US 2005/0109080 A1      May 26, 2005

(30) Foreign Application Priority Data

Nov. 24, 2003   (SE) .................................... 0303102

(51) Int. Cl.
*G01H 3/04*       (2006.01)
(52) U.S. Cl. ........................ 73/579; 73/23.2; 73/24.01; 73/24.06
(58) Field of Classification Search .................. 73/579, 73/23.2, 24.01, 24.06
See application file for complete search history.

(56) References Cited

U.S. PATENT DOCUMENTS

| 5,695,925 | A | * | 12/1997 | Ebersole et al. | ................ | 435/4 |
| 5,756,279 | A | * | 5/1998 | Ebersole et al. | ................ | 435/4 |
| 5,768,937 | A | * | 6/1998 | Wajid et al. | ................ | 73/24.06 |
| 6,247,354 | B1 | * | 6/2001 | Vig et al. | ................ | 73/54.41 |
| 2004/0129056 | A1 | * | 7/2004 | Hok et al. | ................ | 73/24.06 |

OTHER PUBLICATIONS

Strutt et al., "*Theory of Sound*", vol. 2, 2nd Ed. 1896, paperback version, Dover Books, NY, 1945, pp. 18-31.
Morse, "*Thermal Physics*", WA Benjamin, NY 1969, 2nd Ed., pp. 206-209.
Doebelin, "*Measurement Systems: Application and Design*", McGraw-Hill, NY pp. 126-137.
Beranek, "*Acoustics*", McGraw-Hill, NY 1954, pp. 68-69, 136-139.

* cited by examiner

*Primary Examiner*—Hezron Williams
*Assistant Examiner*—Rodney Frank
(74) *Attorney, Agent, or Firm*—Merchant & Gould P.C.

(57) ABSTRACT

The invention is concerned with a method and apparatus for real time analysis of gas mixtures, e g determination of air quality, including at least one resonator (1, 11), means for gas transportation to and from the resonator (1, 11), e g by diffusion or transit flow via openings (5) means for activation (2) and detection (3) of an acoustic signal within the resonator (1, 11), at least one means (7) for measurement of the temperature within the resonator (1, 11), and at least one means (4) for the determination of both the resonance frequency and the quality factor of the resonator (1,11) in real time. These entities are related to the average molecular mass and viscosity or thermal conductivity, respectively, of the gas mixture. The resonator (1, 11 may include a compliant element, e g a constricted volume (6) and an inertial element, e g ist opening (5) or may support standing acoustic waves, in which the sound wavelength is related to a physical dimension of the resonator (1, 11). The determination of resonance frequency and quality factor is preferably based on phase detection within a phase locked loop and is thereby independent of magnitude. In addition to self oscillations at a frequency determined by the resonance frequency, a repetitive frequency modulation is being generated by which a quantity representing the quality factor of the resonator (1, 11) is being generated in real time. Furthermore, means (7) for compensation of temperature or pressure dependence of the resonance frequency or quality factor are included. By an arithmetic-logical unit, e g a microprocessor (9, 17), measured values related to air quality, e g carbon dioxide concentration, relative humidity and temperature are being made available.

17 Claims, 2 Drawing Sheets

REAL TIME ANALYSIS FOR GAS MIXTURES

Figure 1:
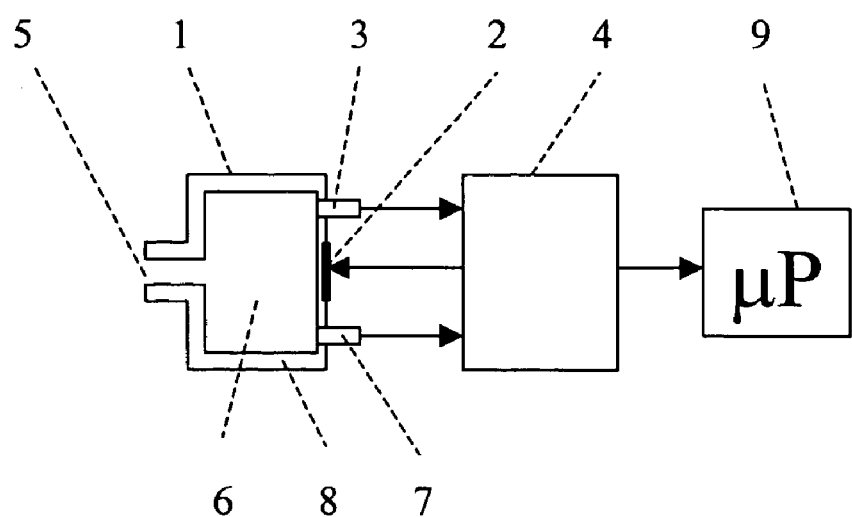

This invention is concerned with a method and apparatus for real time analysis of gas mixtures. Such methods and apparatus are useful e g to protect human beings and animals from harmful gases. They can also be used for controlling or monitoring processes of different kinds, involving emission or assimilation of gases, e g with the objective of minimizing consumption of limited natural resources, including energy. In both these cases, the real time aspect is essential, since the result of the analysis needs to be available continuously, or repeatedly with short time intervals in order for the purpose of the method or apparatus to be fulfilled.

One important application area for the present invention is real time determination of air quality for monitoring and control of indoor environment. Poor air quality is dangerous to health and is detrimental to human performance. Wide international consensus has been achieved that temperature, relative humidity and $CO_2$ concentration are important variables for the determination of air quality. Prolonged or repeated exposure to higher $CO_2$ concentration than 1000 ppm (volume parts per million) should be avoided which should be compared to the background level of fresh air which is approximately 370 ppm at the present (increasing by 2 ppm/year). The corresponding 'window' for acceptable values can be note both for temperature, +18 . . . +25° C., and relative humidity, 30 . . . 70%.

An uncompromising demand on methods and apparatus for real time determination of air quality is signal resolution, repeatability, and accuracy, enabling the tracing of variations with adequate margin. Adequate and sufficiently fast response to changes in air quality is also of utmost importance, as well as user friendliness and reliable function. On the other hand, truly absolute measurements are not always necessary, since it is frequently only of interest to study changes from a certain starting point. Costs with respect to purchase, operation and maintenance should of course be as low as possible, in relation to alternative solutions.

Many methods for gas analysis have been described in the literature, and there are also a number of products available on the market. One of the most versatile tools is mass spectroscopy, enabling identification of volatile molecules and determination of concentration with high accuracy, even at low concentrations. In mass spectroscopy, the sample is first ionized and is thereafter subjected to an electromagnetic field in which its constituents are separated according to the molecular mass. After separation, a detector is performing the necessary operation of providing an output signal representing prevalence in relation the molecular mass. Mass spectroscopy is used as a scientific reference method but due to its high cost and its volume and precision demanding design only had limited laboratory use.

Gas chromatography, like mass spectroscopy, makes use of physical separation of the individual components of a gas mixture. While mass spectroscopy makes se of difference in mass, in gas chromatography the components are separated according to their affinity to a surface of a solid of fluid state, called the stationary phase in contrast to the carrier gas into which the sample is being injected. Gas chromatography is an important analytical instrument but has limitations due to complexity similar to mass spectroscopy.

Absorption spectroscopy in the infrared wavelength area is another useful method to analyze gas mixtures, especially relatively heavy molecules exhibiting distinct absorption peaks within the infrared wavelength range. Such peaks originate from the various quantized vibration or rotation. Many molecular species can be identified by their 'finger print', and it is in certain cases possible to use individual wavelength bands for concentration determination of single gases. Carbon dioxide can e g be detected by its narrow absorption band at 4.3 μm. Infrared spectroscopy is, however, sharing many of the shortcomings mentioned above, and it lacks the versatility of mass spectroscopy.

A further possibility for analysis of gas mixtures is to use the chemical reactivity of gaseous species for classification, identification and quantification. The sample is in this case subjected to a collection of reagents, and the emergence of chemical reactions is detected by e g the generation or take up of heat caused by the reaction, depending on whether it is exothermal or endothermal. Other detection possibilities are pH measurements or position along an axis of oxidation/reduction. Chemical sensors of this kind are frequently designed for non-repetitive use, depending on the evolution of rest products or consumption of reagents. Even in the case of catalytic action from the sensors, I e its function is basically reversible, there is risk for contamination from certain substances, limiting or eliminating the catalytic operation. The usefulness for automatic, time continuous or repetitive measurements is therefore limited.

The use of acoustic measurements for gas analysis has been successful for binary, i e the simplest form of mixtures. According to elementary theory, the velocity of sound c is determined by the following expression (J. W. S. Rayleigh, "The Theory of Sound", vol. 2, $2^{nd}$ Ed. 1896, paperback version, Dover Books, N.Y., 1945, p. 29):

$$c=(kT\gamma/m)^{1/2} \qquad (1)$$

where m is the molecular mass, T the absolute temperature, $k=1.38*10^{-23}$ J/K Boltzmann's constant, and γ is the ratio between the specific heat at constant pressure and volume, respectively.

If the molecular constituents of a gas mixture are known, their relative concentrations can be determined by measuring the velocity of sound. $CO_2$ has a mass of 44 atomic units, compared to the average value of dry air which is 28.95. In other words, increasing carbon dioxide concentration leads to a decrease of the velocity of sound. In an ideal gas mixture, the velocity of sound is determined by the average value of the molecular mass of the included components. If there is also a variation of the γ number, it will also influence, but in general, this variation is considerably smaller than the variation of molecular mass and can therefore often be neglected. Measurements of the velocity of sound can in principle be performed by transmitting a short sound pulse across a known distance, and measuring its transit time. Such equipment is commercially available but requires complimentary equipment in more complex gas mixtures than binary.

It may be concluded that none of the methods mentioned above are useful in the applications mentioned in the introduction, due to shortcomings in either performance or price.

The objective of the present invention is to solve these and related problems. The invention is concerned with a method and apparatus for real time analysis of gas mixtures. The method makes use of relatively complex relations but can be implemented by readily accessible material and components. Furthermore, prerequisites are available for mass production at very low cost. The method makes use of reversible and physically well defined phenomena, requiring a minimum of material and energy. This implicates small costs for installation and maintenance, and very high reliability.

The method and apparatus for gas analysis make use of parallel measurements of one entity related to the velocity of sound in the gas mixture, and one entity related to viscosity. The dynamic and kinematic viscosity of a gas, denoted $\eta$ and $\mu$, respeictively, are given by the following approximate expression (P. M. Morse: Thermal Physics, W A Benjamin, N.Y. 1969, $2^{nd}$ Ed., p. 209):

$$\eta = \mu^* \rho = (8mkT/\pi)^{1/2}/3\sigma_c \qquad (2)$$

where $\rho$ is the gas density, and $\sigma_c$ is the collision cross section, i e the equivalent area that the gas molecule exhibits in collisions with other molecules. The collison cross section is depending on e g the atomic bonds within the molecule, and its affinity of binding to other molecules. As a consequence of this dependence, various well-known gases exhibit variations in viscosity which cannot be related to their molecular mass. It should also be noted that the viscosity of a gas mixture is not necessarily an average viscosity value of the each one of its components.

The combined measurement of two or several measurands related to molecular mass and viscosity adds information not present from any one of these entities. It is thus possible to extract more specific information about a certain gas mixture by such combined measurement. The example of air quality determination includes two independent variables except temperature, namely the concentration of both water vapor and carbon dioxide. Measurement of two variables with known functional relations between these concentrations enables their determination. It is illustrated by the linear equation system (3)-(4) below:

$$m = a_0 + a_1 RH + a_2 X_{CO2} \qquad (3)$$

$$\eta = b_0 + b_1 RH + b_2 X_{CO2} \qquad (4)$$

where RH denotes relative humidity and $X_{CO2}$ the concentration of carbon dioxide, while m and $\eta$ are retained as molecular mass and viscosity, respectively. The measurement of these two entities, and knowing the values of the coefficients $a_i$, $b_i$, i=0, 1, 2 enables the calculation of RH and $X_{CO2}$. The coefficients $a_i$, $b_i$, i=0, 1, 2 are assumed to be known constants, which does not exclude a possible temperature or pressure dependence. Should such dependence prevail, the temperature and pressure could be measured with an independent method, and the dependence could be corrected using well-known techniques. It should be noted that eq. (1) and (2) already include temperature dependence.

In the present invention, one or several acoustic resonators are being used for the measurement of entities related to molecular mass and viscosity. A resonator is basically a second order system with one degree of freedom, characterized by a mass element M, a compliant element K, and a friction element F. Such a system can be described with a second order differential equation according to $$M(d^2y/dt^2) + F(dy/dt) + Ky = A\, x(t) \qquad (5)$$

where dy/dt and $d^2y/dt^2$ are the first and second derivative with respect to time for the one dimensional movement y(t), and Ax(t) represents an externally applied force, partitioned into one time independent amplitude A and a time dependent function x(t). From elementary theory solutions of (5) are known for several cases of x(t), e g step, impulse and sinusoidal inputs.

Equations analog to (5) are being used to describe resonators of many kinds, in which the variable y(t) can represent other entities than the movement of a mass-spring system, e g acoustic and electromagnetic resonators.

Linear second order systems are completely determined by the resonance frequency $f_r$ and the damping ratio $\zeta$ which are related to the coefficients M, F, and K according to the following relations:

$$f_r = 1/2\pi^* (K/M)^{1/2} \qquad (6)$$

$$\zeta = F/(MK)^{1/2} = 1/2Q \qquad (7)$$

The quality factor Q is often used as an alternative quantity when $\zeta$ is small. Q is defined as the ratio between stored and dissipated energy within the resonator. From the relations (6) and (7) it is evident that the (undamped) resonance frequency is only depending on the reactive elements M and K, whereas the damping ratio relates to both the reactive and dissipative elements. With increasing damping ratio (low Q) there is a gradual transition into a first order system. For accurate and independent determination of $f_r$ and Q it is advantageous with as high quality factor as possible. A practical lower limit is Q=1, which corresponds to the stored energy being as large as or larger than the dissipative energy, or that the reactive impedance is larger than the resistive.

The solution to eq. (5) for a sinusoidal input signal is illustrative of the resonant behavior. As described in e g E O Doebelin: "Measurement Systems—Application and Design", McGraw-Hill, N.Y. 1966, p. 134f, the transfer function y(t)/x(t) over the angular frequency $\omega(=2\pi f)$ normalized to the resonance angular frequency $\omega_r(=2\pi f_r)$:

$$y(j\omega)/x(j\omega) = A/k[(j\omega/\omega_r)^2 + (2\zeta j\omega/\omega_r) + 1] \qquad (8).$$

The transfer function can be partitioned in an amplitude corresponding to the absolute value of this complex function, and a phase angle, corresponding to arc tan of the ratio between the imaginary and the real parts. Graphs of this amplitude as a function of frequency may be found in various text books (e g E O Doebelin: "Measurement Systems—Application and Design", McGraw-Hill, N.Y. 1966), illustrating the mutual dependence between e g measurements of amplitude and frequency at maximum oscillations, also given by the following expressions:

$$A_{peak}/A_{low\,freq} = 1/2\zeta(1-\zeta^2)^{1/2} \qquad (9)$$

$$f_{peak} = f_r (1-\zeta^2)^{1/2} \qquad (10).$$

From eq. (9) it is evident that $\zeta$ (and thereby Q) can be calculated by measuring the amplitude ratio $A_{peak}/A_{low\,freq}$, i e the peak amplitude divided by the amplitude at low frequencies. Thereafter, $f_r$ can be calculated from eq. (10). The quality factor Q can also be determined by the relation $$Q = f_r/\Delta f \qquad (11)$$

in which $\Delta f$ denotes the half value frequency width with respect to signal power.

It is also possible to determine $f_r$ and $\zeta$ by measuring the phase angle $\phi(\omega)$ of the signal with respect to the applied signal:

$$\phi(\omega) = \text{arc tan}[2\zeta/(\omega/\omega_r - \omega_r/\omega)] \qquad (12)$$

The singularity occurring at $\omega=\omega_r$ reflects a mathematical property of the arc tan function at $\phi=n\pi/2$, n=1, 3, 5, . . . , which can be avoided by imposing the condition of continuity for a physical quantity. By derivation of this expression with respect to angular frequency, the following expression is obtained:

$$d\phi/d\omega = -1/2\zeta\omega_r^*[(\omega/\omega_r)^2 + 1]/[1 + ((\omega/\omega_r)^2 - 1)^2/4\zeta^2(\omega/\omega_r)^2] \qquad (13)$$

This derivative is negative at all frequencies and reaches a maximum at $\omega=\omega_r$:

$$[d\phi/d\omega]_{\omega=\omega_r}=-1/\zeta\omega_r=-2Q/\omega_r \quad (14)$$

From (12), (13), (14) it is clear that $f_r$ and Q can be determined by phase measurements as an alternative to amplitude measurements. A significant advantage is that the determination is then basically independent of the acoustic signal level. As already mentioned, the accuracy, as well as the separability of the two entities, increases with increasing quality factor.

A simple type of acoustic resonator is built from a compliant element, e g a gas volume V, and an inertial element, e g an opening to this volume determined by its radius a, its cross section area $A=\pi a^2$, and length $\lambda$ (L. Beranek, Acoustics, McGraw-Hill, N.Y., 1954, p 69, 137).

$$\omega_r=2\pi f_r=c^*(A/\lambda V)^{1/2} \quad (15)$$

$$Q=a^*(\omega_r/2\mu)^{1/2} \quad (16)$$

Eq. (15) and (16) can be deduced from eq. (4) and (5) and show that the angular frequency at resonance $\omega_r$ is related to the velocity of sound (and consequently to the molecular mass by eq. (1)), whereas Q is related to the kinematic viscosity $\mu$. A circular cross section of the opening is assumed, since this provides a higher quality factor than other geometries. Determination of $f_r$ and Q is thus enabling the calculation of molecular mass and the viscosity. By adequate dimensioning of the geometry of the resonator, a suitable quiescent point for $f_r$ and Q can be chosen.

The type of resonator described above, frequently called Helmholtz resonator, assumes that geometric dimensions are considerably smaller than the wavelength of sound at the operating frequencies. Acoustic resonators can also utilize sound as a wave phenomenon, whereby reflected, so called standing waves, may give rise to resonance. In this case the geometric dimensioning of the resonator is related to the sound wavelength to fulfil the criterion of standing waves. An example of such a resonator is Kundt's tube, the length L of which in the case of closed end surfaces should equal multiples of half the sound wavelength at resonance, i e:

$$f_r=N^*c/2L, N=1, 2, 3, \ldots \quad (17)$$

The quality factor can in this case either by coupled to viscosity as in eq. (16), or to other mechanisms for attenuation of sound waves, e g the thermal conductivity of the gas which incidentally is known to be related to viscosity.

By the line of reasoning described above, the principle of combined measurements of resonance frequency and quality factor, as well as its applicability for determination of e g relative humidity and carbon dioxide concentration in air by the relations (3) and (4), is deemed to be clarified.

Figure 2:
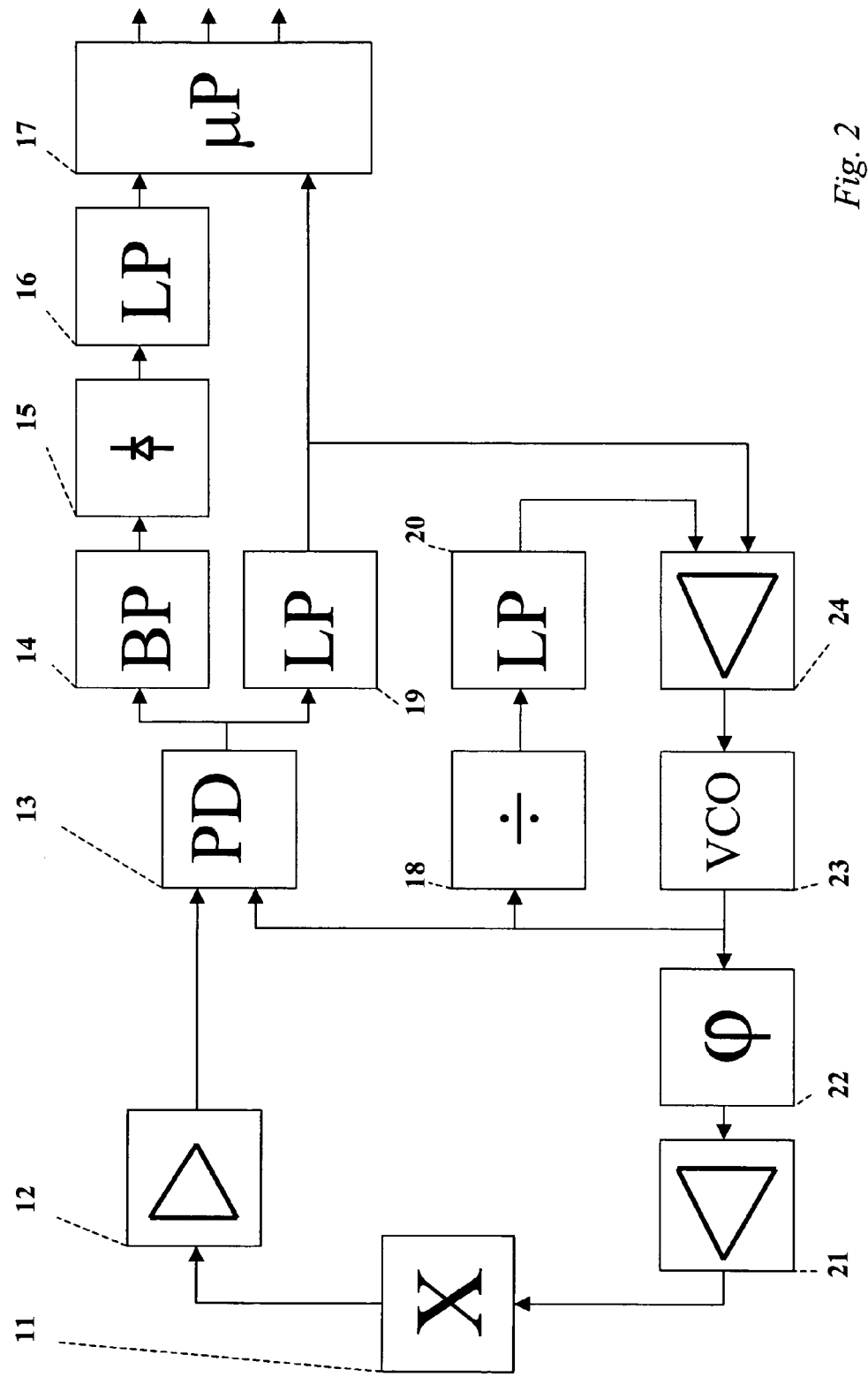

Apparatus enabling the use of the method according to the invention in real time, and its implementation at low cost will be described in connection to the enclosed drawings. FIG. 1 shows a comprehensive block diagram of said apparatus, whereas FIG. 2 depicts functional details in some detail. The figures should be considered as examples of embodiments which can be varied in many different ways within the framework of the enclosed claims.

FIG. 1 shows schematically the apparatus according to the invention. An acoustic resonator 1 is built from a partly closed volume 6 being filled with the gas mixture to be analyzed. The volume 6 is provided with one or several openings 5 which can act as means for active or passive transportation of gas to and from the volume 6. Transportation can e g be controlled by diffusion, or by transit flow between two or several openings within an ambient flow according to well-known principles. It should be noted that opening in this connection includes gas permeable membranes which may be useful to enable gas exchange while avoiding solid particles or pollutants to enter the resonator 1.

In the schematic FIG. 1, the opening 5 is also constituting an inertial element in the acoustic resonator according to the principles described above. The volume 6 together with the opening 5 determine the resonance frequency $f_r$ and the quality factor Q according to eq. (15), (16). The walls 8 of the resonator 1 are preferably stiff, making their mechanical resonance frequencies or eigenfrequencies considerably higher than $f_r$.

The resonance frequency of the resonator 1 may vary over several orders of magnitude between different embodiments, depending on specific demands, from 100 Hz to 10 MHz. The quality factor exhibits smaller variation, from approximately 1 to 100. The physical dimensions of the resonator 1 may also vary depending on the application, from tens of micrometers to tens of millimetres. It could be noted that the resonator may preferably be fabricated by MEMS (Micro Electro Mechanical Systems) technology in which semiconductor materials, e g silicon, is being used in combination with methods for mass production being successfully used for producing integrated circuits.

To the acoustic resonator 1, means for activation 2 and detection 3 are being connected. The activating means 2 is basically a loudspeaker element, and the detection means 3 a microphone. These may be built from electro-acoustic elements using the electrothermal, electrostatic, electrodynamic, piezoelectric or magnetostrictive effects. In a preferred embodiment, the activating means 2 consists of a piezoelectric membrane, e g fabricated from lead zirconate titanate with metallic films according to well-known technology.

In some applications it is possible to use the same element for activation and detection, employing the fact that the acoustic resonator 1 interacts with the impedance of the activating element 2. The detector means 3 is in this case a circuit for measuring the electrical impedance of the activating means 2. Such an embodiment however requires a high quality factor of the resonator 1 which cannot always be achieved. In other embodiments, the means 2, 3 for activation and detection may be positioned at some distance to the resonator, and the signal transfer can take place by acoustic wave propagation in solid, liquid or gas phase.

Functionally it is the task of the activating means 2 to generate an acoustic signal which is converted into an electric signal by the detector 3. At resonance, maximum signal amplitude is detected within the resonator, whereas the amplitude is decreasing at lower and higher frequencies. If activation and detection is performed from outside the resonator, the opposite condition will be valid, the signal amplitude having a minimum at resonance. At resonance there is a shift of the signal phase according to eq. (13) and (14). It is advantageous if the means 2, 3 lack eigenresonances within the frequency range of the acoustic resonator 1, since such could interfere with the function. The detector 3 or another measuring means could preferably also be used for measuring the hydrostatic pressure for compensating the pressure dependence indirectly implicated by eq. (2) and (16). The dynamic viscosity is, like the velocity of sound, basically independent of pressure, while the kinematic viscosity is reversely proportional to density and thereby the hydrostatic pressure.

There is also means for temperature measurement connected to the acoustic resonator 1 for compensation of the temperature dependence described above and to transmit a representative value of the ambient temperature. It is assumed that the connected means 2, 3, and 7 and auxiliary equipment have such small self heating that the measured temperature is representative of the ambient. Should this not be the case, another temperature sensor could be connected to the system. Methods for compensation of undesired influence from e g temperature and pressure, both in the cases of additive or multiplicative dependence (offset error and calibration error, respectively), are well known from other branches of technology. As an alternative to such compensation, thermostat or pressure regulation of the measuring cell could be used, whereby it is certified that the determination of resonance frequency and quality factor is always performed at constant temperature or pressure. A disadvantage is that the complexity of the system increases, along with its power consumption.

The apparatus according to the invention also includes at leats one means 4 for determination of both the resonance frequency and the quality factor of the resonator 1. The means 4 is preferably operating with electrical signals, both for activating the resonator via the activating means 2, and for detection, amplification, filtering etc of the electrical signal coming from the detector 3, and for compensating eventual undesired dependence of temperature, pressure etc. In a typical embodiment, the means 4, constitutes an oscillator together with the resonator 1 and the activating/detecting means 2, 3, the oscillating frequency of which is determined by the resonance frequency of the resonator 1. In addition, the means 4 generates a frequency modulation centred to this frequency, by which the quality factor is determined by any one of the relations (9), (11), and (14). More details about an embodiment of the means 4 will be provided in connection with FIG. 2.

The apparatus according to the invention also includes at least one arithmetic-logic unit 9 in which calculation of entities related to the resonance frequency and quality factor of the resonator 1, e g concentrations of carbon dioxide and water vapour, is performed. The unit 9 preferably consists of an integrated circuit in the form of a programmable microprocessor which in addition to an arithmetic-logic unit also includes analog/digital converter, circuits for serial or parallel digital signal communication, and memory units for temporary or permanent storage of information.

It deserves to be pointed out that the means 4 and the unit 9, as well as other elements may be implemented in many ways within the framework of known technology. In the following, only one embodiment will be described in some detail, which by no means excludes other solutions.

FIG. 2 shows a more detailed block diagram of one embodiment of the apparatus according to the invention. The acoustic resonator including its elements for activation and detection is drawn as one block 11. A buffer amplifier 21 is connected to the activating means and is supplying this element with sufficiently high signal power in order to provide a detectable acoustic signal according to the description above in connection with FIG. 1. Furthermore, another amplifier 12 is connected to the detecting element of the resonator 11. A phase correcting element 22 is also present within this part of the circuit with the purpose of compensating eventual phase deviation in any of the amplifiers 12, 21 or the resonator 11. The phase correcting element 22 consists in the simplest case of a resistor and a capacitor, eventually combined with an active amplifying element. An alternative position of the element 22 is after the amplifier 12 at the detector side of the circuit.

The circuit elements 11, 12, 21, 22 are parts of a phase locked loop (PLL), which also includes a phase detector 13 a low pass filter 19, another amplifier 24 and a voltage controlled oscillator 23. The function of the loop is is such that the phase of the signal from the oscillator 23 is compared to the output signal from the amplifier 12 within the phase detector 13, the output signal of which is fed back to the oscillator 23 after passing the low pass filter 19. The oscillating frequency of the loop 'locks' to the resonance frequency of the resonator 11, possibly with a certain frequency difference depending on eventual phase deviation within the system, which, however, can be compensated by the phase correcting element 22. A typical oscillating frequency is 5–50 kHz, whereas the time constant of the low pass filter is typically 0.1–100 seconds. This time constant is determining the response time to rapid changes of the constitution of the gas mixture, if gas exchange via the means for gas transportation (5) is more rapid.

Means for generating a frequency modulation around the resonance frequency is also included in the apparatus according to the invention. This modulation can e g be a subharmonic of the oscillating frequency, by dividing this frequency in afrequency counter 18 consisting of cascaded flip flop gates according to known technology. After filtering and amplitude control in a low pass filter 20, this signal is added as a small modulation of the input signal to the voltage controlled oscillator 23, via the signal adding operational amplifier 24. The oscillating frequency from the oscillator 23 will then become modulated, i e provide dwith a frequency sweep superposed on the actual oscillating frequency determined by the resonance frequency of the resonator 11. It should be pointed out that a condition for this function is that the time constant of the low pass filter 19 is considerably larger than the period of the frequency sweep, since the modulation would otherwise be fed back. On the other hand, the period of the frequency sweep should be larger than the period of the resonance frequency multiplied by the quality factor of the resonator 11, since otherwise the phase detector would receive a signal from the resonator 11 representing a transient oscillation rather than a stationary harmonic input signal. The frequency modulation should in other words lack sudden changes, and could preferably be sinusoidal. Techniques to generate a sinusoidal waveform from a square wave and vice versa are well known but require in this case attention to phase deviation caused by filtering.

The signal from the phase detector 13 will include a low frequency modulation, synchronous with the frequency sweep according to the discussion above, and with an amplitude determined by the phase sensitivity of the resonator $d\phi/d\omega$, which is related to its quality factor according to eq. (14). This signal is input to a band pass filter 14 with centre frequency at the repetition frequency of the frequency sweep, and a rectifier 15 for converting signal amplitude into a DC voltage via the low pass filter 16.

The output signals from the low pass filters 19 and 16 thus represent the resonance frequency and phase sensitivity, respectively, the latter being related to the quality factor. The digitized signals are input to a programmable arithmetic logical unit 17. The variation of these entities can therefore be monitored in real time with a time resolution determined by the time constants of the low pass filters 16 and 19, or by the response time for gas exchange between the resonator 11 and the ambient. The unit 17 performs calculation of desired entities, e g those related to air quality, such as concentration of carbon dioxide, relative humdity and temperature. The calculations are automatically performed without significant time delay according to an algorithm corresponding to eq. (3), (4), (15), (16), (17) which has been storde in the program memory of the unit 17. For simplicity, the elements for compensation of temperature and/or pressure dependence which were described in connection with FIG. 1 have been excluded in FIG. 2.

All the mentioned circuit elements, including the phase detector 13, the oscillator 23 and the arithmetic-logic unit 17 are commercially available in the form of integrated circuit elements which can be mounted and connected by soldering on a circuit board. It is also possible to integrate all or most of the elements in an application specific integrated circuit (ASIC) which will highly reduce the fabrication cost.

The method and the apparatus according to the invention can be varied in many ways within the framework of the enclosed claims.

The invention claimed is:

1. Apparatus for real time analysis of gas mixtures, comprising at least one acoustic resonator, at least one means for transportation of said gas mixture to and from said resonator, at least one means for activation and detection of at least one acoustic signal within, or in connection to, said resonator, and at least one means for the determination of both the resonance frequency and quality factor, or entity related thereto, from said signal, in real time, wherein said determination of resonance frequency and quality factor is essentially independent of the magnitude of said acoustic signal, being based on phase measurement with at least one phase detector, directly or via another circuit element connected to said means for activation and detection, and said phase measurement includes at least one phase correcting element for compensation of eventual undesirable phase deviation.

2. Apparatus according to claim 1 wherein said resonance frequency of said resonator is a monotonous function of the average molecular mass of said gas mixture within at least one interval, and said quality factor is a monotonous function of the viscosity or heat conductivity of said gas mixture within at least one interval, and said quality factor is larger than one.

3. Apparatus according to claim 1 wherein said resonator includes at least one compliant element, and at least one inertial element, and that the absolute value of the acoustic impedance of said compliant element and inertial element, respectively, exceeds the dissipative acoustic resistance determined by the viscosity of said gas mixture.

4. Apparatus according to claim 1 wherein said resonator supports the emergence of standing acoustic waves within said gas mixture, whereby the sound wavelength at said resonance frequency is related to at least one physical dimension of said resonator, and that said quality factor to a signflcant part is determined by the viscosity or thermal conductivity of said gas mixture.

5. Apparatus according to claim 1 wherein said means for activation and detection include at least one electro-acoustic element employing electrothermal, electrostatic, electrodynamic, piezoelectric, piezoresistive or magnetostrictive effects, and that said means do not exhibit eiagenresonances within the frequency range of said resonator.

6. Apparatus according to claim 1 wherein at least one means for compensation of temperature or pressure dependence of said resonance frequency or quality factor, and that the self heating of said resonator as a consequence of said means and element is neglectible or controllable.

7. Apparatus according to claim 1 wherein at least one amplifying element connected to said means for activation and detection in order to sustain self oscillations, preferably sinusoidal, at a frequency essentially determined by, or identical to, said resonance frequency, and that in addition, a repetitive frequency modulation is being generated around said resonance ferquency, and a quantity related to the quality factor of said resonator is being generated by said frequency modulation, and that the period of said frequency modulation is considerably shorter than the response time of said apparatus with respect to rapid changes of said resonance frequency, and longer than the period of said resonance frequency multiplied by said quality factor.

8. Apparatus according to claim 1 wherein said means including at least one phase locked loop, in which one electrical signal corresponding to said acoustic signal is being first input to at least one phase detector the output signal of which directly or after filtering in a low pass filter controls one voltage controlled oscillator the output of which performs said activation directly or via buffer stages, and electro acoustic activating element and is the second input to said phase detector, and that at least one frequency sweep is input to said voltage controlled oscillator that said frequency sweep with respect to position and magnitude is adapted to said resonance frequency and quality factor, and at least one detector circuit for quantifying the influence of said frequency sweep to the output of said phase detector.

9. Apparatus according to claim 1 wherein at least one arithmetic-logical unit, for performing arithmetic and logical operations on said signals, or signals related to these, whereby measured values corresponding to entities related to air quality are made available.

10. Apparatus according to claim 1, wherein real time analysis of gas mixtures comprises the determination of air quality.

11. Apparatus according to claim 1, wherein said at least one means for transportation of said gas mixture to and from said resonator transports said gas mixture by diffusion or transit flow via one or several openings to said resonator.

12. Apparatus according to claim 3, wherein said at least one compliant element comprises one volume containing said gas mixture and constricted by stiff walls.

13. Apparatus according to claim 3, wherein said at least one inertial element comprises an opening to said volume.

14. Apparatus according to claim 13, wherein said opening has a circular cross section.

15. Apparatus according to claim 7, wherein the repetitive frequency modulation generated around said resonance frequency is in synchronism with said self oscillations.

16. Apparatus according to claim 9, wherein the at least one arithmetic-logical unit comprises a microprocessor.

17. Apparatus according to claim 9, wherein the measured value is corresponding to entities related to air quality comprise carbon dioxide concentration, relative humidity, and temperature.

* * * * *